United States Patent [19]

Hausberg et al.

[11] Patent Number: 4,711,893
[45] Date of Patent: Dec. 8, 1987

[54] USE OF HYDROXYINDOLE DERIVATIVES IN LOWERING BLOOD PRESSURE

[75] Inventors: Hans-Heinrich Hausberg, Ober-Ramstadt; Henning Böttcher; Christoph Seyfried, both of Darmstadt; Rolf Bergmann, Reichelsheim, all of Fed. Rep. of Germany

[73] Assignee: Merck Patent Gesellschaft mit beschrankter Haftung, Darmstadt, Fed. Rep. of Germany

[21] Appl. No.: 907,909

[22] Filed: Sep. 16, 1986

Related U.S. Application Data

[63] Continuation-in-part of Ser. No. 738,329, May 28, 1985, abandoned.

[30] Foreign Application Priority Data

May 28, 1984 [DE] Fed. Rep. of Germany ....... 3419935

[51] Int. Cl.$^4$ ............................................. A61K 31/44
[52] U.S. Cl. .................................................. 514/339
[58] Field of Search ........................................ 514/339

[56] References Cited

U.S. PATENT DOCUMENTS 4,251,538  2/1981  Hausberg et al. .................. 514/323

Primary Examiner—Allen J. Robinson
Attorney, Agent, or Firm—Millen & White

[57] ABSTRACT

Hydroxyindole derivatives of the Formula I

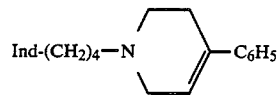

wherein Ind denotes a 4-, 5-, 6- or 7-hydroxyindole-3-yl radical, which can additionally be substituted in the 2-position by alkyl with 1-3 C atoms and/or monosubstituted or disubstituted in the benzene ring by alkyl with 1-3 C atoms, F, Cl, Br and/or CN, and their physiologically acceptable acid addition salts, are effective in lowering blood pressure.

10 Claims, No Drawings

USE OF HYDROXYINDOLE DERIVATIVES IN LOWERING BLOOD PRESSURE

This application is a continuation-in-part of application Ser. No. 738,329, filed May, 28, 1985, now abandoned.

SUMMARY OF THE INVENTION

It is an object of the invention to provide compounds with newly recognized and valuable pharmacological properties, processes for their production and methods for their use.

Upon further study of the specification and appended claims, further objects and advantages of this invention will become apparent to those skilled in the art.

These objects have been achieved by determining that hydroxyindole derivatives of Formula I possess heretofore unrecognized abilities to lower blood pressure.

Thus, the invention relates to the use of hydroxyindole derivatives of Formula I

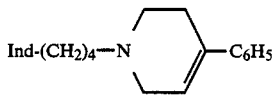

wherein Ind denotes a 4-, 5-, 6- or 7-hydroxyindol-3-yl radical, which can additionally be substituted in the 2-position by alkyl with 1–3 C atoms and/or monosubstituted or disubstituted in the benzene ring by alkyl with 1–3 C atoms, F, Cl, Br and/or CN, and their physiologically acceptable acid addition salts in lowering blood pressure.

DETAILED DISCUSSION OF THE INVENTION

The compounds of the Formula I and their preparation are described in European Patent Application No. 0,007,399.

However, there has been no disclosure nor suggestion in the prior art of any hypotensive action of these substances. In particular, they exhibit hypotensive actions in various forms of increased blood pressure. Specifically, the arterial blood pressure measured directly on conscious spontaneously hypertensive rats (strain SHR/NIH-MO (CHB-EMD)) into which catheters have been inserted (for the method compare J. R. Weeks and J. A. Jones, Proc. Soc. Exptl. Biol. Med. 104, 646–648, 1960), is reduced, as a function of the dose, following a single intragastric administration in a dose range of 0.3–100 mg/kg.

Furthermore, the substances cause dose-dependent lowering of the blood pressure measured at the carotid loop in conscious mongrel dogs (for the method, compare F. H. Page, Science 89, 273–274, 1939) in a 10-day long-term experiment with oral administration of doses which can be less than 10 mg/kg.

The hypotensive properties of these compounds have also been verified on anaesthetized cats by direct measurement of the carotid pressure following intravenous administration of 0.1 mg/kg.

The Ind radical contains the 4-, 5-, 6- or 7-hydroxy group, and preferably is either unsubstituted or contains an additional methyl group or an additional chlorine atom; it preferably represents 5- or 6-hydroxyindol-3-yl, 2-methyl-5- or -6-hydroxyindol-3-yl, 5-hydroxy-6-methylindol-3-yl, 5-methyl-6-hydroxyindol-3-yl, 5-chloro-6-hydroxyindol-3-yl, 5-hydroxy-6-chloroindol-3-yl or 4-hydroxy-7-chloroindol-3-yl.

Of the compounds of the Formula I, the following are particularly preferred as hypotensive compounds:
3-4-(4-phenyl-1,2,3,6-tetrahydropyridyl)-butyl]-5-hydroxyindole [hydrochloride, m.p. 258° C.; methanesulfonate, m.p. 176° (the latter is particularly preferred due to its good solubility and excellent resorption)];
3-4-(4-phenyl-1,2,3,6-tetrahydropyridyl)-butyl]-6-hydroxyindole (hydrochloride, m.p. 271° C.);
2-methyl-3-[4-(4-phenyl-1,2,3,6-tetrahydropyridyl)-butyl]-5-hydroxyindole (hydrochloride, m.p. 255°–257° C.).

The compounds of Formula I can be prepared in a manner which is known, per se, for example, by the processes described in European Patent Application No. 0,007,399, which disclosure is entirely incorporated by reference herein, or by analogous processes. A particularly preferred process is cleavage of corresponding methoxyindole derivatives with the aid of diisobutylaluminum hydride in toluene.

The compounds of the Formula I and their physiologically acceptable salts can be processed to pharmaceutical formulations in accordance with conventional methods of galenic pharmacy. For this, they can be brought into a suitable dosage form together with at least one excipient or auxiliary and, if appropriate, in combination with one or more other active compound(s), e.g., another known antihypertensive agent, such as, f.e., reserpin, methyldopa, clonidin, captopril, labetalol or minoxidil.

These formulations can be employed as medicaments in human or veterinary medicine. Possible excipients are organic or inorganic substances which are suitable for enteral (for example, oral) or parenteral administration and which do not react with the new compounds, for example, water, vegetable oils, benzyl alcohols, polyethylene glycols, gelatine, carbohydrates, such as lactone or starch, magnesium stearate and talc. Tablets, coated tablets, capsules, syrups, elixers, drops or suppositories are used in particular for enteral administration, and solutions, preferably oily or aqueous solutions, and furthermore suspensions, emulsions or implants are used for parenteral administration. The new compounds can also be lyophilized and the resulting lyophilizates can be used, for example, for the preparation of injectable products. The formulations can be sterilized and/or contain auxiliaries, for example, lubricants, preservatives, stabilizers and/or wetting agents, buffers, colorants, flavoring substances and/or aroma substances. If desired, they can also contain one or more other active compounds, for example, one or more vitamins.

The compounds of the Formula I and their physiologically acceptable salts can be used in the therapeutic treatment, e.g., of hypertension, of the human or animal body and in combating diseases, in particular diseases associated with too high a blood pressure, for example, autonomic regulatory disorders with an initial hypertensive status, peripheral circulatory disturbances, cerebrovascular insufficiency and vascular headaches including migraines.

The substances according to the invention are as a rule administered here analogously to known commercially available products (for example, dihydroergocristine), preferably in dosages of about 0.2 to 50 mg, in particular 1 to 10 mg per dosage unit. The daily dosage is preferably about 0.003 to 1 mg/kg of body weight. The low dosages (about 0.2 to 1 mg per dosage unit; about 0.003 to 0.01 mg/kg of body weight) are particularly suitable for use as migraine remedies; dosage of about 1 to 10 mg per dosage unit are preferred for the other indications. However, the specific dose for each particular patient depends on diverse factors, for example, on the efficacy of the specific compound employed, the age, the body weight, the general state of health, the sex, the diet, the time and mode of administration, the rate of excretion, the drug combination and the severity of the particular disease to which the therapy applies. Dosages for a given host can further be determined using conventional considerations, e.g., by customary comparison of the differential activities of the subject compound and a known agent, e.g., by means of an appropriate, conventional pharmacological protocol. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Preparation Example 31 ml of a 20% solution of diisobutylaluminum hydride in toluene are added dropwise to a suspension of 3.46 g of 2-methyl-3-[4-(4-phenyl-1,2,3,6-tetrahydropyridyl)-butyl]-5-methoxyindole in 30 ml of toluene under nitrogen and the mixture is boiled for 3 hours and cooled. Customary working up gives 2-methyl-3-[4-(4-phenyl-1,2,3,6-tetrahydro-pyridyl)-butyl-5-hydroxyindole. Hydrochloride, m.p. 255°–257° C.

3-[4-(4-phenyl-1,2,3,6-tetrahydropyridyl)-butyl]-4-hydroxy-7-chloroindole, m.p. 208°–210° C. is obtained analogously by cleavage of the corresponding 4-methoxy compound.

The examples below relate to pharmaceutical formulations containing compounds of Formula I or their acid addition salts:

EXAMPLE A

Tablets

A mixture of 1 kg of 3-[4-(4-phenyl-1,2,3,6-tetrahydropyridyl-butyl]-5-hydroxyindole hydrochloride, 4 kg of lactose, 1.2 kg of potato starch, 0.2 kg of talc and 0.1 kg of magnesium stearate is pressed to tablets in the usual manner, such that each tablet contains 10 mg of active compound.

EXAMPLE B

Coated Tablets

Tablets are pressed analogously to Example A and are subsequently coated in the customary manner with a coating of sucrose, potato starch, talc, tragacanth and colorant.

EXAMPLE C

Capsules

Hard gelatine capsules are filled with 2 kg of 2-methyl-3-[4-(4-phenyl-1,2,3,6-tetrahydropyridyl)-butyl]-5-hydroxyindole in the customary manner, so that each capsule contains 10 mg of the active compound.

EXAMPLE D

Ampoules

A solution of 1 kg of 3-[8 4-(phenyl-1,2,3,6-tetrahydropyridyl)-butyl]-6-hydroxyindole hydrochloride in 60 l of doubly distilled water is subjected to sterile filtration, filled into ampoules and lyophilized under sterile conditions and the ampoules are filled under sterile conditions. Each ampoule contains 5 mg of active compound.

EXAMPLE E

Ampoules

Analogously to Example D, ampoules are prepared each containing 5 mg of 3-[4-(4-phenyl-1,2,3,6-tetrahydropyridyl)butyl]-5-hydroxyindole methanesulfonate.

Tablets, coated tablets, capsules and ampoules which contain one or more of the other active compounds of Formula I and/or their physiologically acceptable acid addition salts can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of lowering blood pressure in a patient in need of such treatment comprising administering to the patient an effective amount of an hydroxyindole of the formula

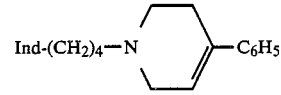

wherein Ind is 4-, 5-, 6- or 7-hydroxyindole-3-yl, or
4-, 5-, 6- or 7-hydroxyindole-3-yl substituted in the 2-position by $C_{1-3}$ alkyl, or monosubstituted or disubstituted in the benzene ring by $C_{1-3}$ alkyl, F, Cl, Br or CN, or
a physiologically acceptable acid addition salt thereof.

2. A method of claim 1, wherein the indole radical is substituted by methyl.

3. A method of claim 1, wherein the indole radical is 5-hydroxyindol-3-yl, 6-hydroxyindol-3-yl, 2-methyl-5-hydroxyindol-3-yl, 2-methyl-6-hydroxyindol-3-yl, 5-hydroxy-6-methylindol-3-yl, 5-methyl-6-hydroxyindol-3-yl, 5-chloro-6-hydroxyindol-3-yl, 5-hydroxy-6-chloroindol-3-yl or 4-hydroxy-7-chloroindol-3-yl.

4. A method of claim 1, wherein the hydroxyindole compound is 3-[4-(4-phenyl-1,2,3,6-tetrahydropyridyl-butyl]-5-hydroxyindole, 3,[4-(4-phenyl-1,2,3,6-tetrahydropyridyl)-butyl]-6-hydroxyindole, 2-methyl-3-[4-(4-phenyl-1,2,3,6-tetrahydropyridyl)-butyl]-5-hydroxyindole, or a hydrochloride thereof.

5. A method of claim 1, wherein the unit dosage is 0.2–50 mg.

6. A method of claim 1, wherein the unit dosage is 1–10 mg.

7. A method of claim 1, wherein the daily dosage is 0.003–1 mg/kg.

8. A method of claim 1 for treating an autonomic regulatory disorder associated with a condition of hypertension in a patient.

9. A method of treating hypertension according to claim 1.

10. A method of claim 1 wherein the hydroxyindole compound is 3-[4-(4-phenyl-1,2,3,6-tetrahydropyridyl)-butyl]-5-hydroxyindole methanesulfonate.

* * * * *